United States Patent
Schröter et al.

(10) Patent No.: US 12,378,179 B2
(45) Date of Patent: Aug. 5, 2025

(54) PROCESS FOR PRODUCTION OF AN ALKOXYLATED PRODUCT

(71) Applicant: BAKELITE GMBH, Iserlohn-Letmathe (DE)

(72) Inventors: Stephan Schröter, Essen (DE); Pravin Kukkala, Louisville, KY (US); Ganapathy Viswanathan, Louisville, KY (US); Sarah Bay, Düsseldorf (DE); Athina Kerkaidou, Iserlohn (DE)

(73) Assignee: BAKELITE GMBH (DE)

( * ) Notice: Subject to any disclaimer, the term of this patent is extended or adjusted under 35 U.S.C. 154(b) by 1237 days.

(21) Appl. No.: 15/733,832

(22) PCT Filed: May 28, 2019

(86) PCT No.: PCT/EP2019/063760
§ 371 (c)(1),
(2) Date: Nov. 30, 2020

(87) PCT Pub. No.: WO2019/229039
PCT Pub. Date: Dec. 5, 2019

(65) Prior Publication Data
US 2021/0214295 A1    Jul. 15, 2021

(30) Foreign Application Priority Data
May 30, 2018   (EP) ..................... 1817505

(51) Int. Cl.
| | | |
|---|---|---|
| *C07C 41/03* | (2006.01) | |
| *C07C 41/16* | (2006.01) | |
| *C08G 18/10* | (2006.01) | |
| *C08G 18/32* | (2006.01) | |
| *C08G 18/66* | (2006.01) | |
| *C08G 65/26* | (2006.01) | |

(52) U.S. Cl.
CPC .............. *C07C 41/03* (2013.01); *C07C 41/16* (2013.01); *C08G 18/10* (2013.01); *C08G 18/3215* (2013.01); *C08G 18/6603* (2013.01); *C08G 65/2612* (2013.01)

(58) Field of Classification Search
CPC ......... C07C 41/03; C07C 41/16; C08G 18/10; C08G 18/3215; C08G 18/6603; C08G 65/2612
See application file for complete search history.

(56) References Cited

U.S. PATENT DOCUMENTS

| | | | |
|---|---|---|---|
| 2,331,265 A * | 10/1943 | Sapp ..................... | C07C 43/205 560/255 |
| 3,803,246 A * | 4/1974 | Rosenzweig et al. ..................... | C08G 63/676 528/219 |
| 5,032,642 A | 7/1991 | Lemon et al. | |
| 5,364,908 A * | 11/1994 | Oishi ..................... | C08G 18/10 525/107 |
| 5,795,933 A | 8/1998 | Sharp et al. | |
| 6,166,151 A * | 12/2000 | Hariharan .............. | C08G 69/44 525/107 |
| 2004/0082713 A1 | 4/2004 | Tutin et al. | |

FOREIGN PATENT DOCUMENTS

| | | |
|---|---|---|
| JP | 2005075938 | 3/2005 |
| JP | 2006273899 | 3/2005 |

* cited by examiner

*Primary Examiner* — Shane Fang
(74) *Attorney, Agent, or Firm* — Edmonds & Cmaidalka, P.C.

(57) ABSTRACT

The invention relates to a process for preparing an alkoxylated product. The aim of the invention is to provide aromatic polyols for preparing polyurethane-based and polyisocyanurate-based polymers, which ensure good miscibility with the isocyanate component and other components, have a good storage stability and render the end product flameproof. For this purpose, the invention devises a process for preparing an alkoxylated product by. reacting bisphenol F with propylene carbonate and/or propylene oxide as propoxylation agent and ethylene carbonate and/or ethylene oxide as ethoxylation agent, the propoxylation agent and the ethoxylation agent being used in a molar ration of 70:30 to 45:55.

8 Claims, No Drawings

PROCESS FOR PRODUCTION OF AN ALKOXYLATED PRODUCT

In the production of polyurethanes and polyisocyanurates isocyanates are crosslinked by a polyaddition reaction using polyols. The isocyanates comprise at least two —NCO groups and the polyols at least two reactive —OH groups (polyhydric alcohols). Polymers are formed which depending on their chemical or morphological construction may exhibit thermoplastic, elastic or thermosetting properties. Accordingly, polyurethanes and polyisocyanurates have a very wide field of application, for example for foams (rigid or flexible), coatings, adhesives, elastomers, insulations and composite materials. Particularly in the search for energy- and resource-efficient materials, polyurethanes and polyisocyanurates are particularly important on account of easy-to-realize light weight construction.

The production of polyurethanes and polyisocyanurates is effected by mixing polyols with isocyanates, thus causing the system to start to gel after a short time. It will be appreciated that the components need to be matched to one another in terms of their viscosities in order to achieve high degree of mixing that results in homogeneous products having desired properties. Properties of the end product are substantially determined by the chain length and degree of branching of the polyol component and combinations of different polyols are therefore often employed, for example polyether polyols and polyester polyols, to optimize processing and properties.

During the production of typical rigid polyurethane foams, the highly exothermic reaction between polyols and isocyanates leads to internal scorching. This phenomenon adversely affects the physical properties of the foam and increases the potential for causing problems with respect to the flammability.

Moreover, the use of hydrocarbon based organic blowing agents further increases the flammability of the finished foams. Consequently, flame retardant additives are added in the formulation, wherein these are generally halogenated compounds. However, many such flame-retardants pose threat to the environment. Hence, it is desirable to use polyols that are inherently flame resistant, which will enhance the thermal and fire performance of the polyurethane (PUR) and polyisocyanurate (PIR) foams and potentially minimize the amounts of these environmentally and expensive flame retardant additives in the formulation.

Alkoxylated bisphenols are known for the production of polyurethanes. Thus, EP 0 763 067 Bi describes the use of alkoxylated bisphenols for the production of hot melt adhesives and EP 2 743 285 A1 for coated conducting elements. It is further apparent from EP 1 851 261 B1 that one component of a two-component polyurethane composition for structural adhesives may be an ethoxylated or propoxylated aromatic diol in combination with aliphatic triols.

It has further been found that aromatic diol typs polyols based on bisphenol A have only insufficient suitability for the production of polyurethanes since they are solid substances which is very disadvantageous in terms of process engineering and in addition also have poor heat resistance.

It has also been found that the use of both pure ethoxylated bisphenol F and pure propoxylated bisphenol F as aromatic polyether polyols for the production of polyurethanes face some serious challenges. This is because both are pasty substances which are not pumpable at 20-30° C. and thus do not have the desired processability in polyurethane production. Melting of the ethoxylated bisphenol F or of the propoxylated bisphenol F entails an energy input into the system which is also not desired. Furthermore, attempts at solubalizing pure ethoxylated bisphenol F and also pure propoxylated bisphenol F had the result that they could hardly be dissolved in suitable solvents since they had a ready propensity for crystallization.

It is accordingly an object of the present invention to provide aromatic polyols for the production of polyurethane- and polyisocyanurate-based polymers which ensure good miscibility with the isocyanate component and further components, exhibit good storage stability and impart the end product with good flame retardancy, thus making it possible to eschew the use of halogenated compounds.

This object is achieved according to the invention by a process for the production of an alkoxylated product by reaction of bisphenol F with propylene carbonate and/or propylene oxide as a propoxylating agent and ethylene carbonate and/or ethylene oxide as an ethoxylating agent, wherein the propoxylating agent and the ethoxylating agent are used in a molar ratio of 70:30 to 45:55.

Alkoxylated bisphenol F formed by reaction of an ethoxylating agent and a propoxylating agent with bisphenol F constitutes a co-condensate according to the present application.

It is preferable to use per one mol of bisphenol F, 1.6 mol to 0.9 mol of propoxylating agent and 1.6 mol to 0.9 mol of ethoxylating agent, preferably in turn 1.3 mol to 1.0 mol of propoxylating agent and 1.3 mol to 1.0 mol of ethoxylating agent. It has been found that a molar ratio of bisphenol F:the sum of propoxylating agent and ethoxylating agent of for example 1:2.0 to 1:3.2 has a positive influence on the storage stability of the co-condensate both in pure form and in solution.

A particularly surprising effect in respect of storage stability both in pure form and in solvents was achieved at a molar ratio of bisphenol F propoxylating agent:ethoxylating agent of 1:1:1.

The bisphenol Fused for the production of alkoxylated bisphenol F is known from the prior art. It is thus produced by reaction of phenol with formaldehyde under acidic conditions.

This affords an isomer mixture of o-o', o-p and p-p' bisphenol F which depending on the reaction conditions and production processes can vary in its composition. The hydroxyl functionality of the produced bisphenol Fis at least 2.

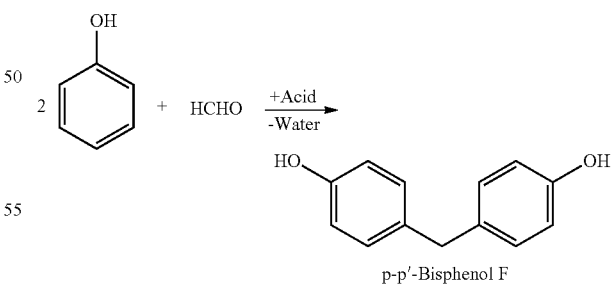

p-p'-Bisphenol F

Reaction of the bisphenol F with propoxylating agents, such as propylene oxide and/or propylene carbonate, and with ethoxylating agents, such as ethylene oxide and/or ethylene carbonate, in a molar ratio of 70:30 to 45:55, preferably 50:50, affords the alkoxylated bisphenol F. Since the reaction with ethylene oxide/propylene oxide, which are in the gaseous state, must be effected in a pressure reactor, which involves more process engineering effort, it is preferable to employ ethylene carbonate as the ethoxylating agent/propylene carbonate as the propoxylating agent.

The reaction shall be elucidated using the example of p-p' bisphenol F:

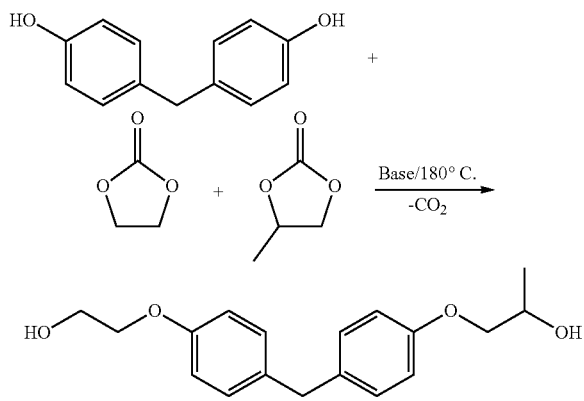

On account of the different isomers of bisphenol F and their difunctionality corresponding isomers of the alkoxylated bisphenol F are also formed. In particular, the use of propylene oxide and/or propylene carbonate causes further isomers to be formed since two different carbon atoms are capable of reaction. Furthermore, stereoisomers may be formed.

The alkoxylation reaction is generally performed in an alkaline medium at temperatures between 120° C. and 200° C. Generally, the bisphenol F is initially charged, melted and addition of an alkaline medium in the form of for example potassium carbonate, sodium carbonate, potassium hydroxide, sodium hydroxide, potassium alkoxides, sodium alkoxides, calcium hydroxide, calcium oxide, amines or triphenylphosphine is effected with stirring at temperatures up to for example about 200° C. Subsequently the propoxylating agent and the ethoxylating agent are added and, depending on technical capability, the carbon dioxide formed is discharged. It is immaterial to the properties of the alkoxylated product whether the propoxylating agent is added at the same time or at different times or in admixture with the ethoxylating agent. However, the reaction time of the alkoxylation was shortened when the propoxylating agent, in particular propylene carbonate, was reacted with the bisphenol F first.

The alkoxylated product formed is optionally distilled under vacuum to reduce the water content/free propoxylating agent and/or ethoxylating agent content and after cooling may optionally be neutralized with an acid. A neutral product is preferred in the use as a polyol in polyurethane production. Preference is given to a neutralization for example with a compatible organic (for example benzoic acid, phthalic acid, lactic acid, anthranilic acid or salicylic acid) and/or inorganic acid (for example hydrochloric acid, sulfuric acid, phosphoric acid or nitric acid).

It is generally also possible to perform the production of bisphenol F by reaction of phenol with formaldehyde in a reactor and to undertake the reaction with the propoxylating agent and the ethoxylating agent immediately thereafter preferably in the same reaction vessel. This has the advantage that the bisphenol F need not be subjected to storage and may put to further use immediately as required.

Surprisingly, the alkoxylated product produced according to the invention shows an exceptional solubility in solvents particularly compatible with the production of polyurethanes. Thus the alkoxylated product is excellent soluble in for example organo phosphates such as triethyl phosphate and diphenylcresyl phosphate, 1,4-butanediol, alkoxylated resorcinol such as propoxylated resorcinol, polyether polyols such as ethoxylated sugar, aromatic polyester polyols, modified or unmodified phenolic resoles (e.g. phenol and cresol based resoles) either alone or mixtures thereof. The resoles can be those that are dissolved in organic solvents.

Surprisingly, the propensity for crystallization of the alkoxylated product produced according to the invention compared to solutions containing pure ethoxylated bisphenol F or propoxylated bisphenol F is very low/not present. It was particularly surprising that the reaction of bisphenol F with propylene carbonate and/or propylene oxide as the propoxylating agent and ethylene carbonate and/or ethylene oxide as the ethoxylating agent, wherein the propoxylating agent and the ethoxylating agent are present in a molar ratio of 70:30 to 45:55, exceeds the storage stability of both the alkoxylated product and a solution thereof many times over compared to when the molar ratio is outside the claimed range. In addition, as a result of its high aromatic proportion, the product produced according to the invention imparts the end product with a higher flame retardancy and compatibility with diisocyanates (for example MDI) or polyisocyanates (for example p-MDI) and with blowing agents.

The alkoxylated product was preferably added in a weight ratio to the solvent of 90:10 to 10:90, preferably 60:40 to 40:60, preferably in turn 50:50. Particularly at an alkoxylated product produced according to the process of the invention:solvent ratio of 50:50 a very good storage stability over several weeks was achieved in various solvents.

Alkoxylated resorcinol has proven particularly as solvent. The term "alkoxylated resorcinol" encompasses substances where the resorcinol has been reacted with at least one alkoxylating agent, thus for example an ethoxylating agent (ethylene oxide, ethylene carbonate) and/or propoxylating agent (propyl ene oxide, propylene carbonate). The molar ratio of resorcinol to alkoxylating agent is preferably 1:2 to 1:2.5.

Alkoxylated resorcinol comprehends for example the following structure:

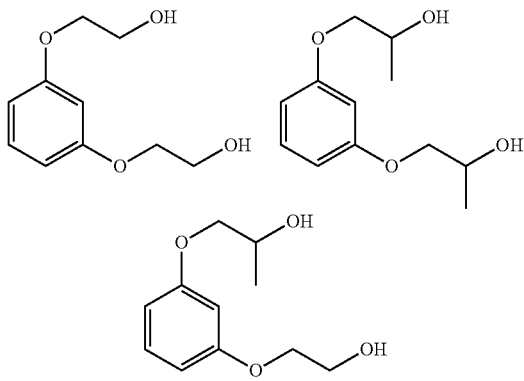

wherein these products are formed mainly in the reaction of resorcinol with ethylene carbonate and propylene carbonate. However, further products may also be formed in particular in the reaction with propylene carbonate since in propylene carbonate two different carbon atoms are attacked. Likewise, different stereoisomers are formed in the reaction with propylene carbonate.

It is particularly preferable when a combination of an ethoxylating agent and a propoxylating agent is used as the alkoxylating agent. A resorcinol alkoxylated in this way was a more effective solvent of the product alkoxylated according to the invention than for example pure propoxylated resorcinol.

The production of the alkoxylated resorcinol may be effected such that the resorcinol is melted and in an alkaline medium in the form of for example potassium carbonate, sodium carbonate, potassium hydroxide, sodium hydroxide, potassium alkoxides, sodium alkoxides, calcium hydroxide, calcium oxide, amines or triphenylphosphine at elevated temperatures is admixed with a first alkoxylating agent (for example propylene carbonate) and the reaction takes place with removal of carbon dioxide. This may optionally be followed for example by addition of a further alkoxylating agent (for example ethylene carbonate) at elevated temperature, wherein the carbon dioxide is in turn removed. After appropriate postreaction the product may optionally be distilled off and neutralized with an acid (for example benzoic acid, phthalic acid, lactic acid, anthranilic acid, salicylic acid, hydrochloric acid, sulfuric acid, phosphoric acid and/or nitric acid).

The use of alkoxylated resorcinol as solvent is advantageous in particular in the production of polyurethanes since additional difunctional groups which can react with diisocyanates are present. The viscosity of the overall polyol mixture is simultaneously reduced. Furthermore, the use of alkoxylated resorcinol increases the aromatic proportion of the polyol component and the flame retardancy and compatibility for example with MDI or the blowing agents was therefore further increased.

It is advantageous in terms of process engineering when during the production of the product alkoxylated according to the invention the resorcinol is alkoxylated simultaneously or subsequently utilizing the same reaction vessel. This allows for example a polyol component suitable for reaction with polyisocyanates on account of its functionality and viscosity to be provided in simple fashion. On account of its exceptional storage stability this polyol component may be provided as required.

It is generally also possible for the alkoxylated product produced according to the invention to be used as one polyol component alone or in combination with a solvent and for further polyol components to be used for the production of polyurethanes/polyisocyanurates, such as for example polyester polyols. Polyester polyols comprise reaction products of polyols, typically dials, with polycarboxylic acids or their anhydrides, typically dicarboxylic acids or dicarboxylic anhydrides. The polycarboxylic acids or anhydrides may be aliphatic, cycloaliphatic, aromatic and/or heterocyclic. Compared to polyester polyols the product produced according to the invention has a higher thermal stability.

Mannich base polyols which are synthesized from Mannich bases may also be used as part of the isocyanate-reactive compound.

Preferably employed as isocyanate component are m-phenylene diisocyanate, toluene 2,4-diisocyanate, toluene 2,6-diisocyanate, hexamethylene 1,6-diisocyanate, tetramethylene 1,4-diisocyanate, cyclohexane 1,4-diisocyanate, hexahydrotoluene diisocyanate, naphthylene 1,5-diisocyanate, methoxyphenyl 2,4-diisocyanate, diphenylmethane 4,4'-diisocyanate, 4,4'-biphenylene diisocyanate, 3,3'-dimethoxy-4,4'-biphenyl diisocyanate, 3,3'-dimethyl-4,4'-biphenyl diisocyanate, 3,3'-dimethyldiphenylmethane 4,4'-diisocyanate, 4,4',4"-triphenylmethane triisocyanate, a polymethylenepolyphenyl isocyanate, polymeric diphenylmethane diisocyanate (PMDI), isophorone diisocyanate, 2,4,6-toluene triisocyanate and 4,4'-dimethyldiphenylmethane 2, 2',5,5'-tetraisocyanate. In different embodiments the polyisocyanate is diphenylmethane 4,4'-diisocyanate, diphenylmethane 2,4-diisocyanate, hexamethylene 1,6-diisocyanate, isophorone diisocyanate, toluene 2,4-diisocyanate, toluene 2,6-diisocyanate or mixtures thereof. Diphenylmethane 4,4'-diisocyanate, diphenylmethane 2,4-diisocyanate and mixtures thereof are generally referred to as MDI. Toluene 2,4-diisocyanate, toluene 2,6-diisocyanate and mixtures thereof are generally referred to as TDI.

The product produced according to the invention exhibits a good compatibility with MDI or p-MDI in particular even at room temperature while the use of purely ethoxylated bisphenol F requires higher temperatures.

Each of the abovementioned polyisocyanates may be modified such that urethane, urea, biuret, carbodiimide, allophanate, uretonimine, isocyanurate, amide or similar moieties are included. Examples of modified isocyanates of this kind comprise various urethane- and/or urea-containing prepolymers and so-called "liquid MDI" products and the like. It is also possible for the polyisocyanate to be a blocked isocyanate.

Depending on the specific type of the produced polymer and the necessary properties of the polymer a great multiplicity of additional materials may be present during the reaction of the polyisocyanate compound with the product produced according to the invention. These materials comprise but are not limited to surfactants, blowing agents, cell openers, fillers, pigments and/or dyes, drying agent s, reinforcers, biocides, preservatives, antioxidant s, diluents, flame retardants and the like. When a flame retardant is present the flame retardant may be a phosphorus-containing flame retardant. Examples for phosphorus-containing flame retardants comprise but are not limited to triethyl phosphate (TEP}, triphenyl phosphate (TPP), trischloroisopropyl phosphate (TCPP), dimethylpropane phosphate, resorcinol bis (diphenyl phosphate}(RDP}, bisphenol-A diphenyl phosphate (BADP) and tricresyl phosphate (TCP), dimethylmethyl phosphonate (DMM P}, diphenylcresyl phosphate and aluminium diethyl phosphinate. However, according to the invention additional flame retardants may be essentially eschewed on account of the high aromatic proportion of the alkoxylated product.

Examples of diluents comprise polyglycols such as ethylene glycol, glycerol or diethylene glycol, etherified polyglycols such as monomethyl ethers of ethylene glycol or dimethyl ethers of ethylene glycol and dibasic esters of acids such as diethyl adipate, dimethyl adipate, diethyl succinate or dimethyl succinate. Mixtures of any of these diluents may likewise be used.

The relative amounts of polyisocyanate and of the product produced according to the invention are selected to generate a polymer. The ratio of these components is generally referred to as the "isocyanate index" which is to be understood as meaning 100 times the ratio of isocyanate groups to isocyanate-reactive groups provided by the product produced according to the invent ion. The isocyanate index is generally at least 50 and may be up to 1000 or more. Inflexible polymers such as structural polyurethanes and rigid foams are typically produced using an isocyanate index of 90 to 200. When flexible or semi-flexible polymers are produced, the isocyanate index is generally 70 to 125. Polymers containing isocyanurate groups are often produced with isocyanate indices of at least 150 to 600 or more.

To form the polymer the polyisocyanate compound and the alkoxylated product produced according to the invention are mixed and cured. The curing step is achieved by subjecting the reaction mixture to conditions sufficient to bring the polyisocyanate compound and the alkoxylated product to reaction to form the polymer.

In various embodiments the polyisocyanate and the product produced according to the invention—preferably dissolved in solvents—may also contain a catalyst. Examples of catalysts include but are not limited to tertiary amines, such as dimethylbenzylamine, 1,8-diaza(5.4.0)undec-7-ane, pentamethyldiethylenetriamine, dimethylcyclohexylamine and triethylenediamine. Potassium salts, such as potassium acetate and potassium octoate, may likewise be used as catalysts.

The product produced according to the invention may preferably be used for the production of polyurethanes and polyisocyanurates, in particular polyurethanes in the form of prepolymers, foams (rigid, flexible), coatings, lacquers, elastomers, adhesives, sealants and/or composite materials.

The invention shall be more particularly elucidated with reference to an exemplary embodiment:

a) Production of alkoxylated bisphenol F (ABF)
Molar ratio of bisphenol F:propylene carbonate:ethylene carbonate=1:1:1
1. 66.64 kg of bisphenol F are added into a reactor as a solid and melted at temperatures between 120° C.-160° C.
2. 0.17 kg of potassium carbonate are subsequently added with stirring at 130° C. and the reaction mixture is heated further to 175° C.-180° C.
3. 33.98 kg of propylene carbonate are then added over 2.5 h with stirring at 175-180° C. Carbon dioxide is liberated. The feed may optionally be prolonged depending on technical capability for removing the carbon dioxide.
4. 29.30 kg of ethylene carbonate are then added over 2.5 h with stirring at 175-180° C. Carbon dioxide is liberated. The feed may optionally be prolonged depending on technical capability for removing the carbon dioxide.
5. For the postreaction the temperature is held at 175° C. to 180° C. for 1-4 hours, optionally also longer, until no more carbon dioxide is formed and the reaction is complete.
6. The free water, ethylene carbonate and propylene carbonate content are optionally determined.
7. To undertake any desired reduction of the water, ethylene carbonate and propylene carbonate content the reaction mixture is distilled under vacuum for 15 minutes.
8. The reaction mixture is heated to 140° C. and 0.3 kg of salicylic acid are added.
9. When the product has cooled further (45° C. to 50° C.) it may be discharged through a filter. The product is liquid.

b) Production of the alkoxylated resorcinol (molar ratio of resorcinol:propylene carbonate:ethylene carbonate=1:1.0:1.0)
1. 516.7 kg of resorcinol are added as a solid into a reactor and melted (mp: 111° C.).
2. 1.31 kg of potassium carbonate are subsequently added with stirring at 130° C. and the reaction mixture is heated further to 175° C.-180° C.
3. 479.1 kg of propylene carbonate are then added over 2.5 h with stirring at 175-180° C. Carbon dioxide is liberated. The feed may optionally be prolonged for to up to 5 h depending on technical capability for removing the carbon dioxide.
4. 413.4 kg of ethylene carbonate are then added over 2.5 h with stirring at 175-180° C. Carbon dioxide is liberated in turn. The feed may optionally be prolonged to 5 h depending on technical capability for removing the carbon dioxide.
5. For the postreaction the temperature is held at 175° C. to 180° C. for 2-6 hours, optionally also longer, until no more carbon dioxide is formed and the reaction is complete.
6. The reaction mixture is distilled for a short time under vacuum at 175-180° C.
7. The reaction mixture is cooled to 140° C. and 2.58 kg of salicylic acid are added.

The alkoxylated bisphenol F produced at a) was produced using the molar ratio of propylene carbonate:ethylene carbonate=50:50. The obtained properties were recorded under heading VI of Table 1. The remaining products listed in Table 1 were produced according to procedure a), wherein the inventive ratio of propoxylating agent and ethoxylating agent was observed in the production of I, IV, V, VI and VII.

The alkoxylated bisphenol Fs exhibited a low viscosity necessary for polyurethane production. These are also substantially neutral products as a result of which they are likewise suitable for use for production of polyurethanes.

Also surprising was the storage stability of the inventively produced alkoxylated bisphenol F (I, IV, V, VI, VII). To this end, all samples were placed in a conditioning cabinet at 20° C. in pure form. In the noninventively produced samples II, III, VIII-XII crystallisation set in after just a few days making them unsuitable for the production of polyurethanes.

The stability of the inventively produced alkoxylated bisphenol F in solvent too was demonstrably markedly better than for samples II, III, VIII-XII.

To this end a mixture of alkoxylated bisphenol F {sample VI— produced according to a)) and triethylphosphate {TEP) in a weight ratio of 80:20 was prepared and likewise placed in a conditioning cabinet at 20° C. Here too it was shown that only the inventively produced alkoxylated products provided the solution exhibiting the desired storage stability over several weeks.

To complement this further mixtures of inventively alkoxylated bisphenol F {sample VI—produced according to a)), were produced in Table 2 with various solvents in the mentioned weight ratios and stored at 20° C. in a conditioning cabinet. The results are reported in Table 2 and demonstrate persuasively the storage stability of the mixtures, wherein visual assessment of crystallization was used as the measure for storage stability.

TABLE 1

|  | I (inv) | II | III | IV (inv) | V (inv) | VI (inv) | VII (inv) | VIII | IX | X | XI | XII |
|---|---|---|---|---|---|---|---|---|---|---|---|---|
| Molar ratio BPF:PC:EC | 1:1.05:1.05 | 1:1.8:0.2 | 1:1.5:0.5 | 1:1.3:0.7 | 1:1.2:0.8 | 1:1:1 | 1:1.3:1.3 | 1:0.8:1.2 | 1:0.7:1.3 | 1:0.5:1.5 | 1:0.4:1.6 | 1:0.2:1.8 |
| Ratio PC:EC | 50:50 | 90:10 | 75:25 | 65:35 | 60:40 | 50:50 | 50:50 | 40:60 | 35:65 | 25:75 | 20:80 | 10:90 |

TABLE 1-continued

|  | I (inv) | II | III | IV (inv) | V (inv) | VI (inv) | VII (inv) | VIII | IX | X | XI | XII |
|---|---|---|---|---|---|---|---|---|---|---|---|---|
| Viscosity 2s·c [mPas] | 55680 | 280000 | 179200 | 230400 | 140800 | 130000 | 40960 | 133120 | 128000 | 140800 | 368640 | 149758 |
| Viscosity so·c [mPas] | 1260 | 2500 | 2200 | 2320 | 2040 | 1800 | 6720 | 1920 | 1720 | 1840 | 2040 | 1277 |
| Stability 80% in TEP at 2o·c | X | 1 day | 3 days | about 4 weeks | 2.5 weeks | 9 weeks | >9 weeks | 3 days | <1 week | 3 days | 1 day | 2 days |
| Stability pure at 20° C. | 2 weeks | 1 day | 3 days | about 13 weeks | 2.5 weeks | 10 weeks | >10 weeks | 3 days | <1 week | 3 days | 1 day | 2 days |

TABLE 2

| Solvent (SV) | Weight ratio ABF:SV | Storage at 20° C. [in weeks] | | | | | |
|---|---|---|---|---|---|---|---|
| | | 1 | 2 | 3 | 4 | 5 | 6 |
| | | | | crystallization | | | |
| Triethyl phosphate (TEP) | 70:30 | 0% | 0% | 0% | 0% | 0% | 0% |
| | 50:50 | 0% | 0% | 0% | 0% | 0% | 0% |
| Diethylene glycol (DEG) | 70:30 | 0% | 0% | 0% | 0% | 0% | 0% |
| | 50:50 | 0% | 0% | 0% | 0% | 0% | 0% |
| TEP/DEG | 70:30 | 0% | 0% | 0% | 0% | 0% | 0% |
| Ethoxylated sugar (Su-EO) | 70:30 | 0% | 0% | 0% | 0% | 0% | 0% |
| | 50:50 | 0% | 0% | 0% | 0% | 1% | 1% |
| Alkoxylated resorcinol | 70:30 | 0% | 0% | 0% | 0% | 0% | 0% |
| | 50:50 | 0% | 0% | 0% | 0% | 0% | 0% |
| 1,4-butanediol | 70:30 | 0% | 0% | 0% | 0% | 0% | 0% |
| | 50:50 | 0% | 0% | 0% | 0% | 0% | 0% |
| Aromatic polyester polyol Stepan 1812 | 70:30 | 0% | 0% | 0% | 0% | 0% | 0% |
| | 50:50 | 0% | 0% | 0% | 0% | 0% | 0% |
| Aromatic polyester polyol Stepan 2412 | 70:30 | 0% | 0% | 0% | 0% | 0% | 0% |
| | 50:50 | 0% | 0% | 0% | 0% | 0% | 0% |
| Dibasic ester (DBE) | 70:30 | 0% | 0% | 0% | 0% | 0% | 0% |
| | 50:50 | 0% | 0% | 0% | 0% | 0% | 0% |
| Diphenyl cresyl phosphate (DPCP) | 70:30 | 0% | 0% | 0% | 0% | 1% | 1% |
| | 50:50 | 0% | 0% | 0% | 0% | 1% | 1% |
| Cresol-Resol, SO % in DEG | 90:10 | 0% | 0% | 0% | 0% | 0% | 0% |
| | 75:25 | 0% | 0% | 0% | 0% | 0% | 0% |
| | 50:50 | 0% | 0% | 0% | 0% | 0% | 0% |
| Cresol-Resol, 50% in DEG/TEP 1:1 | 75:25 | 0% | 0% | 0% | 0% | 0% | 0% |
| | 50:50 | 0% | 0% | 0% | 0% | 0% | 0% |
| Phenol-Resol, 50% in DEG/TEP 1:1 | 90:10 | 0% | 0% | 0% | 0% | 0% | 0% |
| | 75:25 | 0% | 0% | 0% | 0% | 0% | 0% |
| | 50:50 | 0% | 0% | 0% | 0% | 0% | 0% |

As a result of the high aromatic proportion of the inventively produced alkoxylated product and optionally also as a result of the use of alkoxylated resorcinol which further increases the aromatic proportion, a good flame retardancy in the polyurethane end product was achieved and the compatibility with MDI/with the blowing agents was further increased as well. The additional use of halogenated flame retardants was accordingly eschewed.

What is claimed is:

1. A process for making an alkoxylated product; comprising:
   reacting bisphenol F, a propoxylating agent comprising propylene carbonate and/or propylene oxide and an ethoxylating agent comprising ethylene carbonate and/or ethylene oxide at conditions sufficient to produce an alkoxylated bisphenol F product,
   wherein the propoxylating agent and the ethoxylating agent have a molar ratio of 70:30 to 45:55.

2. The process of claim 1, wherein based on one mol of bisphenol F 1.6 mol to 0.9 mol of propoxylating agent and 1.6 mol to 0.9 mol of ethoxylating agent are used.

3. The process of claim 2, wherein the reaction is based on one mol of bisphenol F, 1.3 mol to 1 mol of propoxylating agent, and 1.3 mol to 1.0 mol of ethoxylating agent.

4. The process of claim 3, wherein the molar ratio between bisphenol F:propoxylating agent:ethoxylating agent is essentially equal to 1:1:1.

5. The process of claim 1 wherein the propoxylating agent comprises propylene carbonate.

6. The process of claim 1 wherein the ethoxylating agent comprises-ethylene carbonate.

7. The process of claim 1 wherein the reaction is effected in an alkaline medium at temperatures of 120° C. to 200° C.

8. The process of claim 1 wherein the addition of propylene carbonate and ethylene carbonate is effected at different times.

* * * * *